United States Patent [19]
Alex et al.

[11] Patent Number: 5,931,814
[45] Date of Patent: Aug. 3, 1999

[54] DERMALLY AFFIXED INJECTION DEVICE

[75] Inventors: Rainer Alex, Bad Krozingen, Germany; Paul Hadvary, Biel-Benken; Hansjörg Tschirky, Ettingen, both of Switzerland

[73] Assignee: Hoffmann-La Roche Inc., Nutley, N.J.

[21] Appl. No.: 08/854,503

[22] Filed: May 12, 1997

Related U.S. Application Data

[63] Continuation of application No. 08/542,760, Oct. 13, 1995, abandoned.

[30] Foreign Application Priority Data

Oct. 28, 1994 [CH] Switzerland .............................. 3227/94

[51] Int. Cl.⁶ ...................................................... A61M 5/14
[52] U.S. Cl. ............................................................. 604/131
[58] Field of Search ...................................... 604/158, 164, 604/131, 136, 138, 141, 142, 145, 147, 153, 156, 157, 180

[56] References Cited

U.S. PATENT DOCUMENTS

| | | |
|---|---|---|
| 4,393,870 | 7/1983 | Wagner . |
| 4,725,265 | 2/1988 | Sairenji . |
| 4,808,168 | 2/1989 | Warring .................................. 604/158 |
| 4,813,426 | 3/1989 | Haber et al. ............................ 604/198 |
| 4,886,499 | 12/1989 | Cirelli et al. . |
| 4,906,236 | 3/1990 | Alberts et al. .......................... 604/164 |
| 5,776,106 | 7/1998 | Matyas .................................... 604/180 |

FOREIGN PATENT DOCUMENTS 272 530  12/1987  European Pat. Off. .

*Primary Examiner*—Manuel Mendez
*Attorney, Agent, or Firm*—George W. Johnston; William H. Epstein; John P. Parise

[57] ABSTRACT

An improved injection device has a casing containing an active substance reservoir, a cannula communicating with the reservoir, a device for inserting the cannula, and pump means for discharging the reservoir contents through the cannula. The cannula 11 is fixed relative to the casing and projects beyond the underside of the casing to the depth required for injection. The cannula is surrounded by a protective element which is moved by a spring drive from a first end position in which the protective device projects beyond the underside of the casing and beyond the cannula to a second end position in which the protective device does not project beyond the underside of the casing.

15 Claims, 2 Drawing Sheets

DERMALLY AFFIXED INJECTION DEVICE

This is a continuation, of application Ser. No. 08/542,760, filed Oct. 13, 1995, now abandoned.

BACKGROUND OF THE INVENTION

1. Field

The invention relates generally to injection devices, and specifically to injection devices having both a contact surface for attaching to a patient's skin and a cannula for piercing the patient's skin and introducing an injection fluid into the patient.

2. Description

As used throughout the specification, the term "injection" will encompass both relatively fast injection (bolus) and relatively slow introduction (occasionally called infusion or instillation) of a liquid into the body.

An injection device of the above kind is known in the art, for example from EP-A-272 530 which corresponds to U.S. Pat. No. 4,886,499, issued Dec. 11, 1989 to Cirelli, et al., the contents of which are herein incorporated by reference. Cirelli, et al. describes various embodiments of such an injection device which utilize various types of reservoirs and pumps. A common feature of all of Cirelli, et al.'s described embodiments is that the mechanical construction results in a device requiring a certain minimum overall height. A very small overall height is necessary for achieving acceptance by patients of devices worn on their bodies.

Another disadvantage of known injection devices in which the injection cannula is shot into the patient's skin is that the liquid connection between the cannula and the reservoir is prone to faults. These faults occur because of the relatively complicated construction needed to permit relative movement between the cannula and the reservoir. Such complicated construction also causes problems with regard to sterility and aseptic filling, especially with heat-sensitive preparations. Moreover, complicated connections of this type, in addition to being prone to breakdown, are so expensive as to make the devices unsuitable as throwaway articles.

Alternatively, if the reservoir and the cannula were to be fixedly connected, the entire reservoir would need to be accelerated for shooting the cannula into the skin, thus requiring far more driving power. Such a solution would therefore be uneconomic. Moreover, disposable or throwaway articles are preferable in many medical applications because it is often difficult to avoid premature discharge of injection solution or, conversely, suction of a small amount of blood, lymph, or the like.

Finally, known injection devices have no simple, reliable means for preventing damage to the cannula when the device is removed from the patient after the injection process.

A need exists for an injection device which does not have these disadvantages, and the subject invention addresses this need.

SUMMARY OF THE INVENTION

The subject invention improves individual components of the device and the co-operation of the components to achieve a desired reduction in overall height, simplification of mechanical operation, and avoidance of damage to the cannula. According to the invention, the above problems are solved by an injection device having the features disclosed hereinbelow.

The subject injection device for introducing an injection fluid into a patient through the patient's skin comprises a casing, a cannula, a protective element, and a drive means for moving the protective element. The casing has a contact surface for contacting a patient's skin. Typically, this contact surface is coated with an adhesive. The cannula is fixedly positioned relative to the casing. The cannula has a tip which is configured and dimensioned for piercing the patient's skin and introducing an injection fluid into the patient. The tip projects beyond the contact surface of the casing toward the patient's skin. The protective element is movable from a first position to a second position. In the first position, the protective element extends beyond the tip of the cannula (shielding the tip of the cannula from the patient's skin). In the second position, the protective element is retracted into the casing (exposing the tip of the cannula to the patient's skin). Typically, the protective device is formed as a sleeve or cup spring. The drive means moves the protective element from the first position to the second position.

In preferred embodiments, the inventive device employs a reservoir for containing the injection fluid. Of particular merit is an integrally formed component having a combined protective sheath, cannula, and reservoir. Such a component can be manufactured by conventional blow-fill-seal technology.

BRIEF DESCRIPTION OF THE FIGURES

An exemplified embodiment of the invention will now be described with reference to the accompanying drawings in which.

DETAILED DESCRIPTION OF THE INVENTION

The invention will now be described in terms of its preferred embodiments. These embodiments are set forth to aid in understanding the invention, but are not to be construed as limiting.

The exemplified embodiments are described with reference to the drawings. These embodiments are of injection devices which can be worn and operated by the patient. As described above, injection devices of this general type are known. One aim of the present invention is to insert an injection cannula into a patient substantially without pain to the patient, thus avoiding the natural reluctance of the patient to injection. Insertion is advantageously brought about by a spring drive according to the present invention.

The term "cannula" as used herein is equivalent to the term "infusion needle" as used in U.S. Pat. No. 4,886,499. Likewise, the term "casing" as used herein is equivalent to the term "housing" as used in U.S. Pat. No. 4,886,499.

In contrast to known devices, in the present inventive device the cannula is inserted by the thrust of the spring drive, but is not moved relative to the casing and the reservoir towards the patient's skin. Rather, the skin moves towards the cannula which is stationary relative the casing and to the reservoir. A protective ring which surrounds the cannula and projects beyond the bottom of the casing holds the skin both away from the cannula and under tension. To insert the cannula, the protective ring is retracted preferably by spring force into the casing. The resulting exposed skin thus moves relative to the cannula and is penetrated by its tip. It has surprisingly been found that the skin, contrary to expectation, is sufficiently accelerated during this process to be penetrated by the cannula. It was also surprising found that this form of penetration by the cannula is practically painless, even up to or at greater depths of penetration than possible with similar known devices.

Figure 1:
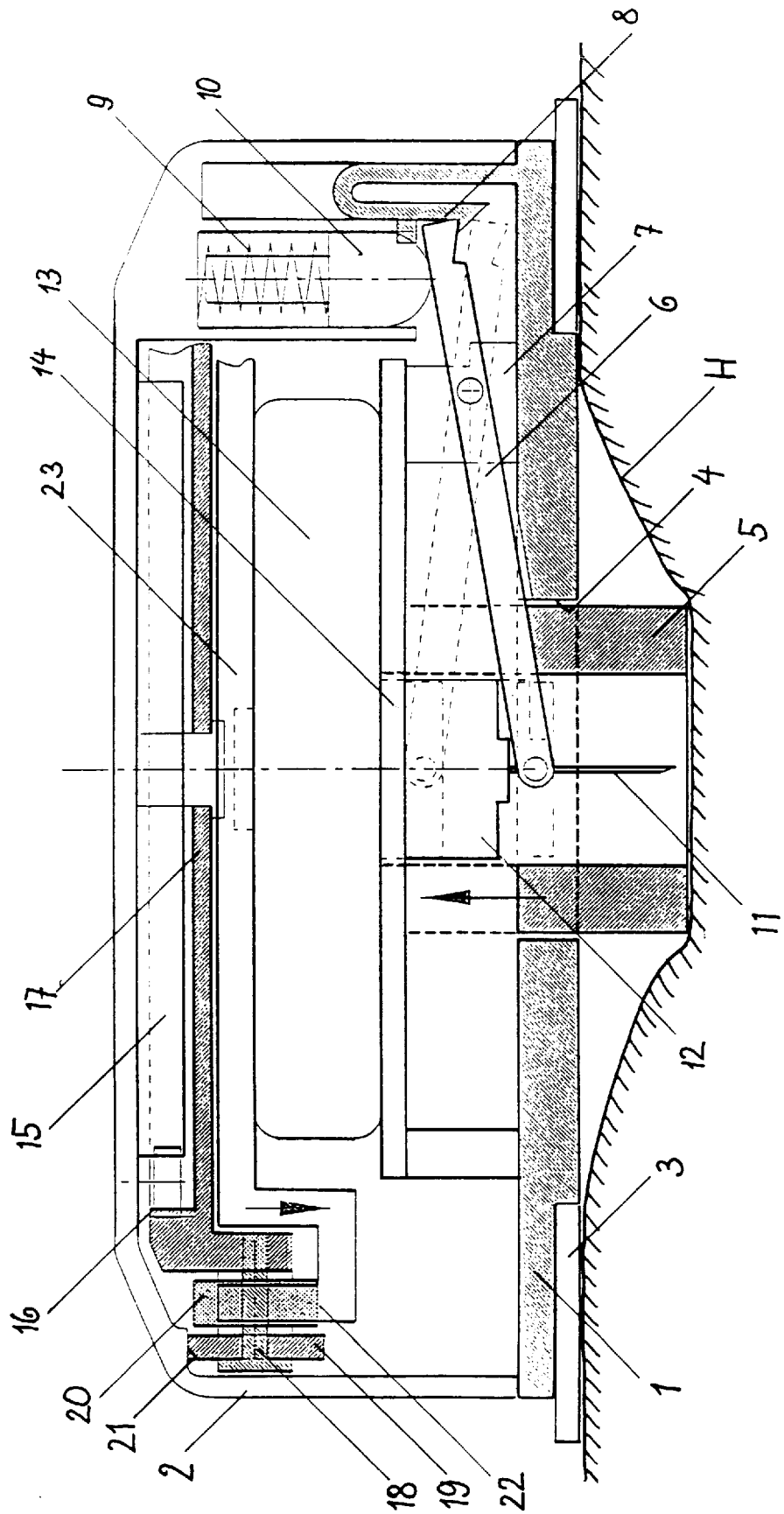
FIG. 1 is a diagrammatic sectional view of an injection device according to one embodiment of the invention.

FIG. 1 shows an injection device of this kind in section, comprising a casing made up of a disc-like baseplate 1 and a cap 2 rotatable relative thereto. On its underside, the baseplate has an annular adhesive layer 3 for securing the device to a patient's skin H. The baseplate 1 has a central concentric opening 4. A cylindrical protective sleeve 5 is disposed in the opening and is axially movable between the extended position (shown) and the withdrawn position (shown by dotted lines), in which the lower end face of the ring 5 is in the same plane as the underside of the base-plate 1.

For the purpose of axial movement, the protective sleeve is connected to one end of a number of two-armed or fork-shaped levers 6 (for example three levers), one of which is shown in FIG. 1. The centers of rotation of the levers 6 are on supports 7 which are fixedly mounted to cap 2. The other ends of the levers, in the position shown, extend into catches 8. Spiral springs 9, which are stressed in the inoperative position, exert spring force on the locked ends of the levers, via short pistons 10.

A cannula 11 is disposed at the center of the opening and rests in a holder 12 which is connected to and forms a structural unit with the wall of a flat approximately cylindrical flexible reservoir 13. The reservoir rests on a subframe comprising a plate 14 held by the supports 7. The reservoir 13, the cannula holder 12 and the cannula 11 are thus fixed relative to the casing. The cannula 11 projects beyond the baseplate by the depth required for insertion. The protective sleeve is dimensioned and disposed so that in the inoperative position it projects sufficiently beyond the cannula 11 to prevent accidental contact with the cannula tip.

The device and the protective sleeve 5, in the extended position for protecting the cannula, is secured by the adhesive layer 3 to the desired or a suitable position on the patient's skin H. The sleeve 5 keeps the skin H away from the baseplate in the manner shown.

The catch 8 can be released by rotating the cap 2 relatively to the baseplate 1. The spring and the piston then press the released lever arm downwards. The other lever arm thus brings the sleeve into the chain-line position, that is, retracted into the casing. The skin H thus exposed moves towards the baseplate and is pierced by the cannula tip, so that the cannula 11 penetrates the skin.

The contents of the reservoir 13 are discharged through the cannula 11 into the patient's skin tissue by a rotary ring 17 moved by an electric motor 15 comprising a drive (for example, a clockwork drive) via a gear 16. Pairs of rollers 19, 20 mounted on common spindles 18 are disposed at uniform angular intervals on the outside of the ring 17. The outer rollers 19 run on a shoulder 21 formed on the inside of the cap 2, while the inner rollers 20 run on wedge shaped inclines 22 on a pressure plate 23. In this manner, by continuous rotation of the ring 17, the pressure plate 23 is slowly moved downwards, so that it compresses the reservoir and conveys the contents thereof through the cannula.

Instead of rollers running on inclines, inclines in opposite directions facing one another can be provided on the rotary ring and on the pressure plate. This construction is simpler, but has the disadvantage that, owing to the sliding friction, the force is greater than that required for rolling friction.

Another possibility for emptying the reservoir is to use a gas-producing cell for exerting a pressure on the reservoir for a specific time. Alternatively, other drives or kinds of reservoirs, as known in the prior art, can be employed.

The reservoir can be emptied either continuously, or in accordance with the measured amount required, for example with respect to the concentration of the active substance or other parameters. To this end, the cannula 11 can be connected to a mini-sensor for insulin, glucose, or the like, which is also inserted into the tissue. Alternatively, a sensor with a second cannula present in the device and similarly inserted, or at another place remote from the device, can be disposed at a suitable measurement site. The motor is provided accordingly with a control device and means for receiving the sensor signals.

Before the device is taken off the patient, the cap can be additionally rotated so as to move the ends of the levers back into the catches, so that the protective sleeve is again extended into the position for protecting the cannula.

Figure 2:
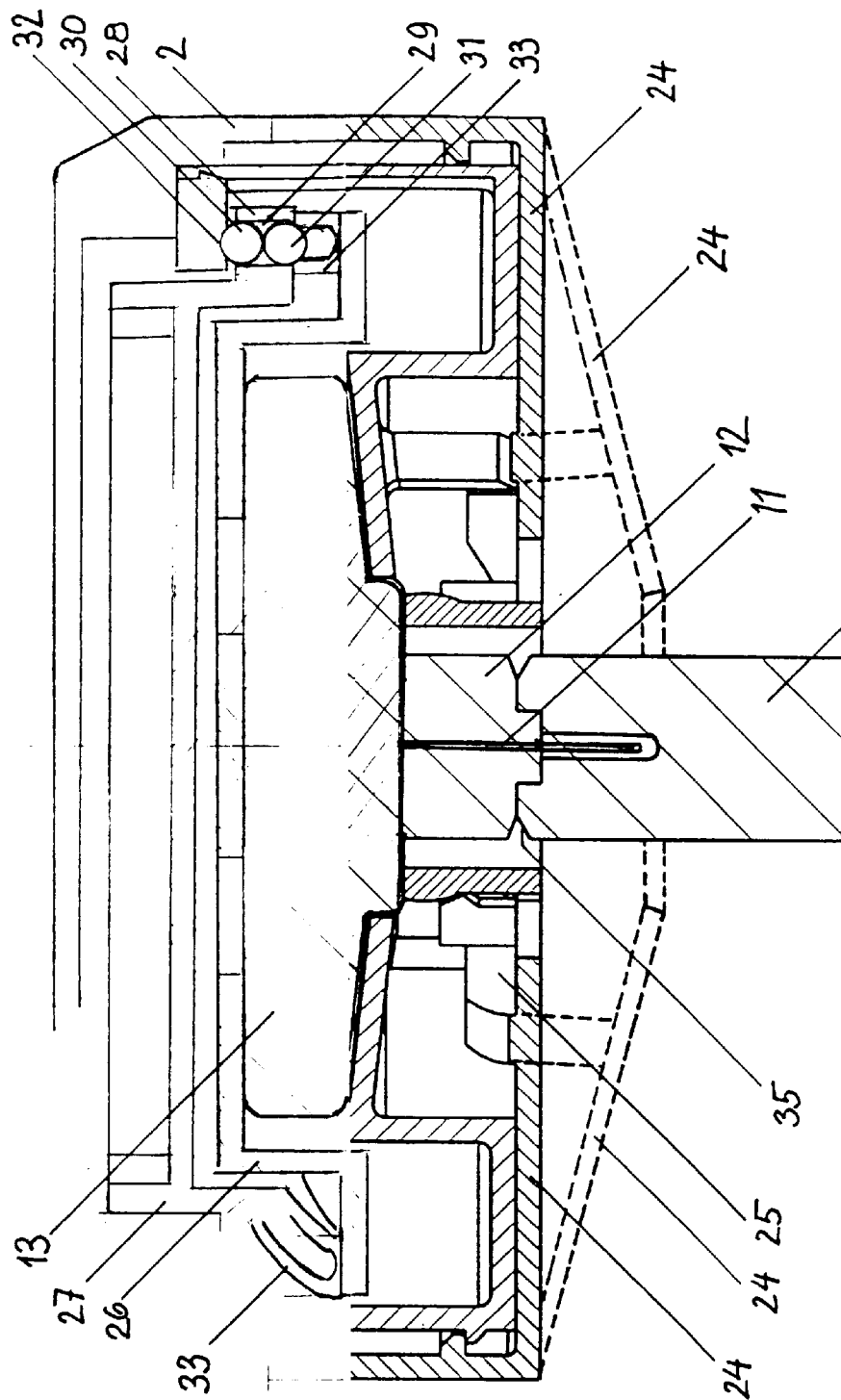
FIG. 2 is a diagrammatic sectional view of an alternative embodiment of the invention.

In FIG. 2, parts corresponding to FIG. 1 are given the same reference numbers. The embodiment in FIG. 2 does not have a protective ring. Instead, the base 24 of the device is in the form of a cup spring which is bent by pressure elements 25 into a prestressed shape (shown by chain lines) in which it projects beyond the cannula tip and thus prevents accidental contact therewith. When the pressure elements 25 are relaxed, the base 24 snaps into its flat inoperative position, so that the patient's skin moves against the cannula in the same manner as in the previously described embodiment.

In this embodiment also, the cup spring forming the base of the device can be brought back to the prestressed position by the pressure elements before being removed from the patient, so as to protect the cannula.

The embodiment in FIG. 2 also shows an alternative solution as regards moving the pressure plate 26 by means of the rotary ring 27. The ring has a flange 28 with three bores 29 at equal angular intervals. Each bore contains two balls 30 and 31, the upper ball 30 bearing against a shoulder 32 secured to the casing and the lower ball 31 running on an incline 33. The sloping surfaces of the inclines 33 have channel-like recesses for guiding the balls 31. As in the first embodiment described, the pressure plate 26 is slowly moved downwards by continuous rotation of the ring 27, so that the plate compresses the reservoir and conveys its contents through the cannula.

The embodiment in FIG. 2 also shows a solution as regards the requirement that the cannula 11 and the contents of the reservoir 13 must be sterile. To this end, a protector 34 for the cannula 11 is integrally formed on the cannula-holder or on the reservoir. Preferably, the cannula 11 with holder 12 is molded and the protector 34 is formed at the same time as the reservoir 13. Moreover the reservoir is formed and filled with the injection fluid, the cannula and holder are put in place and the reservoir is closed in one continuous process known as blow-fill-seal technology. Before the device is placed on the patient's skin, the protector is removed from the cannula 11. To this end, an intentional breaking point 35 is provided between the protector 34 and the cannula-holder 12.

Upon reading this specification, various alternative embodiments will become obvious to the skilled artisan. For example, the drive means for moving the protective element could be via numerous chemical, mechanical, or electrical devices. Likewise, a plurality of cannulas or reservoirs can be employed. Some suggestions for modifications can be found in U.S. Pat. No. 4,886,499, the contents of which are herein incorporated by reference. These variations are to be considered within the scope and spirit of the invention which is only to be limited by the claims which follow and their equivalents.

What is claimed is:

1. An injection device for introducing an injection fluid into a patient through the patient's skin, which comprises:

(a) a casing having an adhesive contact surface for contacting the patient's skin and adhering the casing to the patient's skin;

(b) a cannula fixedly positioned relative to the casing, the cannula having a tip configured and dimensioned for piercing the patient's skin and introducing the injection fluid into a patient, the tip projecting beyond the contact surface of the casing toward the patient's skin;

(c) a protective element movable from a first position to a second position, the first position being such that the protective element extends beyond the tip of the cannula thereby shielding the tip of the cannula from the patient's skin and the second position being such that the protective element is retracted into the casing thereby exposing the tip of the cannula to the patient's skin; and (d) a drive means for moving the protective element from the first position to the second position.

2. The injection device according to claim 1 further comprising:

(i) a reservoir for injection fluid arranged within the casing and fluidly connected with the cannula, and (ii) a pump for pumping the injection fluid from the reservoir to the cannula.

3. The injection device according to claim 2, wherein the reservoir is a shallow cylindrical, flexible receptacle.

4. The injection device according to claim 1 further comprising a feed line for supplying the injection fluid and connecting means for attaching the feed line to the device.

5. The injection device according to claim 1, wherein the protective element is a sleeve which is moveable by a spring drive means such that in the first position the sleeve projects from the casing and in the second position the sleeve is completely inside the casing.

6. The injection device according to claim 5, wherein the sleeve is cylindrical.

7. The injection device according to claim 1, wherein the casing has a base, the drive means comprises pressure elements, and the protective element comprises the casing base in the form of a cup spring, the cup spring being configured and dimensioned so that in the first position it is brought by pressure elements into a pre-stressed shape in which it projects beyond the cannula tip.

8. The injection device according to claim 1, wherein the contact surface is provided with an adhesive.

9. The injection device according to claim 1, wherein the protective element is provided with an adhesive.

10. The injection device according to claim 1 further comprising a protective sheath which forms an integral component together with the cannula and the reservoir.

11. The injection device according to claim 4 further comprising a protective sheath which forms an integral component together with the cannula and the reservoir.

12. The injection device according to claim 11, wherein the integrally formed reservoir, cannula and protective sheath is manufactured by blow-fill-seal technology.

13. The injection device according to claim 11, wherein the device is reusable and the integrally formed reservoir, cannula and protective sheath is replaceable.

14. The injection device according to claim 1 further comprising a sensor.

15. The injection device according to claim 1, wherein the distance which the tip of the cannula projects beyond the contact surface of the casing corresponds to the depth of cannula insertion when the device is operated on the patient.

* * * * *